(12) United States Patent
Quarder et al.

(10) Patent No.: US 8,114,623 B2
(45) Date of Patent: Feb. 14, 2012

(54) METHOD FOR DETERMINING GLUCOSE CONCENTRATION IN TISSUE FLUID

(75) Inventors: Ortrud Quarder, Heidelberg (DE); Stefano Ferrari, Bucks (GB); Peter Stephan, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1015 days.

(21) Appl. No.: 11/936,569

(22) Filed: Nov. 7, 2007

(65) Prior Publication Data

US 2008/0153118 A1 Jun. 26, 2008

Related U.S. Application Data

(63) Continuation of application No. PCT/EP2006/004179, filed on May 4, 2006.

(30) Foreign Application Priority Data

May 7, 2005 (EP) .................................. 05009986

(51) Int. Cl.
*C12Q 1/54* (2006.01)
*C12M 1/34* (2006.01)

(52) U.S. Cl. ....................... 435/14; 435/287.1

(58) Field of Classification Search .......................... None
See application file for complete search history.

(56) References Cited

U.S. PATENT DOCUMENTS

| 5,097,834 | A | 3/1992 | Skrabal |
| 5,118,473 | A | 6/1992 | Coleman et al. |
| 5,243,982 | A | 9/1993 | Mostl et al. |
| 5,640,954 | A | 6/1997 | Pfeiffer et al. |
| 6,048,514 | A * | 4/2000 | Young et al. ................. 424/9.2 |
| 6,852,500 | B1 | 2/2005 | Hoss et al. |
| 7,022,071 | B2 | 4/2006 | Schaupp et al. |
| 7,383,069 | B2 * | 6/2008 | Ruchti et al. ................. 600/331 |

FOREIGN PATENT DOCUMENTS

| DE | 4123441 A1 | 1/1992 |
| EP | 0367752 A | 5/1990 |
| EP | 0534074 B1 | 3/1993 |
| EP | 1072222 A | 1/2001 |
| EP | 0664989 B1 | 7/2002 |
| WO | WO-03/003911 | 1/2003 |

OTHER PUBLICATIONS

International Preliminary Report on Patentability for PCT/EP2006/004179 issued by the International Bureau of WIPO on Dec. 13, 2007.

* cited by examiner

*Primary Examiner* — David Naff
(74) *Attorney, Agent, or Firm* — Baker & Daniels LLP

(57) ABSTRACT

The invention relates to a method and a device for determining the glucose concentration in tissue fluid whereby test values for glucose and for an endogenous reference substance are detected in a sample liquid obtained by microdialysis, microperfusion or ultrafiltration, and the glucose value is corrected in accordance with the test value for the reference substance. The recovery rate for glucose is determined from a non-linear relationship with the recovery rate for the ionic reference substance, and the test value for glucose is corrected therewith. In addition, the concentration of lactate and/or pyruvate is used as a further reference substance in the sample liquid to make further corrections.

4 Claims, 4 Drawing Sheets

METHOD FOR DETERMINING GLUCOSE CONCENTRATION IN TISSUE FLUID

BACKGROUND

1. Field of the Invention

The invention concerns a method for determining the glucose concentration in tissue fluid in which test values for glucose and for an endogenous reference substance are detected in a sample liquid obtained from a body tissue by microdialysis, microperfusion or ultrafiltration and the test value for glucose is corrected in accordance with the test value for the reference substance. The invention also concerns a corresponding device.

2. Description of the Prior Art

Body tissue consisting of cells in a liquid environment in which metabolic products are transported between the cells and the blood vessels. In order to monitor glucose of diabetic patients, for example, it is possible to insert a probe into tissue for long periods in order to continuously obtain components from the tissue fluid by means of diffusion processes and to determine the glucose content in the tissue from the effusate. This can correlate closely with the blood glucose content without requiring an invasive access to the blood circulation. The measurement can take place outside of the body in which case the sample liquid is applied to a sensor. In this connection an ionic reference technique is known in which an ionic reference value and in particular $Na^+$ is detected simultaneously with glucose by an ion-selective electrode in order to calibrate the recovery of the glucose in the dialysate. In this case, it is assumed that the known concentration of the reference substance in the body fluid is substantially invariant. A prerequisite of the known evaluation methods is that there is a strict linear relationship between the recovery of the endogenous calibrator and glucose in the sample liquid. However, empirical comparative measurements make this seem doubtful.

SUMMARY OF THE INVENTION

The invention considers local effects in the tissue as well as transport resistances which occur due to the special probes that are used for microdialysis, microperfusion or ultrafiltration. Accordingly, in embodiments of the invention, the concentration of lactate and/or pyruvate as a reference substance is determined in the sample liquid. This enables the specific metabolic paths of glucose degradation to be utilized in order to draw conclusions about effects on the measurement correction that are due to local tissue reactions.

A concentration ratio of lactate to pyruvate in the sample liquid is advantageously determined to correct the test value for glucose. In embodiments of the invention, at a concentration ratio of lactate to pyruvate in a selected middle range of between about 10:1 and about 20:1, a linear correction dependent on the concentration ratio is carried out, and in a higher range above the selected range and above a concentration ratio of 20:1 the test value for glucose is corrected by a constant. An analogous correction is also conceivable when using lactate alone as the reference substance.

In embodiments of the invention, the recovery rate ($R_{GLU}$) for glucose is determined from a non-linear relationship with the recovery rate ($R_{REF}$) for the ionic reference substance, and the test value for glucose is corrected therewith. In this manner it is possible to carry out a type of technical correction in a specifically adapted form for effects that are caused mainly by the specific probe technology, for example, due to the membrane processes. This allows for an accurate correction.

This may be due to the fact that the recovery of the ion reference is higher than that of glucose due to the small particle size and/or due to the charge, as may be the case with rapid perfusion. Hence the non-linear compensation curve runs in a curve shape below the bisecting line.

According to embodiments of the invention, the recovery rate ($R_{GLU}$) for glucose is determined according to the relationship $$1-R_{REF}=(1-R_{GLU})^k$$

in which k is a predetermined value. In this connection, the value k can be determined empirically as the ratio of resistances for the transfer of glucose and the reference substance between tissue fluid and sample liquid. Furthermore, it is proposed that the recovery rate ($R_{REF}$) for the reference substance is determined as the ratio of the test value for the reference substance in the sample liquid and a constant concentration value in the tissue fluid. Sodium is advantageously used as an endogenous ionic reference substance.

A particularly effective and accurate compensation can be achieved by using sodium as a reference substance for a correction of deviations due to the measurement technology and lactate and/or pyruvate as a reference substance for a correction of locally-related deviations of the test value for glucose in the sample liquid from the actual glucose concentration in the tissue of the organism.

The compensation described above can be used particularly advantageously in procedures in which a probe located in the tissue is used to obtain sample liquid by perfusion with rinsing liquid or by applying a negative pressure.

An additional functionality is achieved by means of the fact that a malfunction is signalized when an upper and/or lower predetermined threshold of the test value for the reference substance is exceeded.

The above-mentioned process may be achieved utilizing a corresponding device for carrying out the process. Accordingly a sensor unit is provided for a device where said sensor unit is designed to determine the concentration of lactate and/or pyruvate as a reference substance in the sample liquid.

In embodiments of the invention, the evaluation unit has an evaluation program which determines the recovery rate ($R_{GLU}$) for glucose from a non-linear relationship with the recovery rate ($R_{REF}$) for the ionic reference substance, and the test value for glucose is corrected therewith.

BRIEF DESCRIPTION OF THE DRAWINGS

The above-mentioned and other features of this invention and the manner of obtaining them will become more apparent and the invention itself will be better understood by reference to the following description of an embodiment of the present invention taken in conjunction with the accompanying drawings, wherein.

Figure 1:
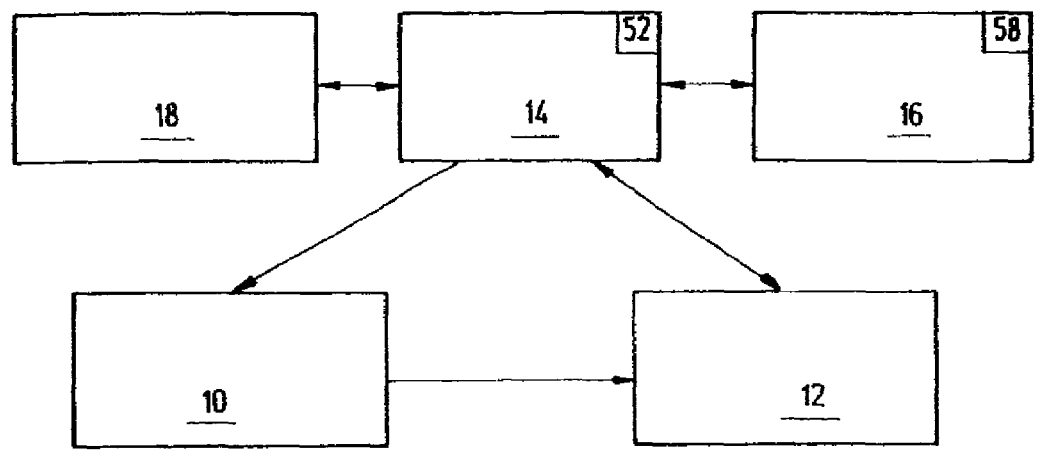
FIG. 1 shows a block diagram of a measuring arrangement for determining glucose.

Although the drawings represent embodiments of various features and components according to the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

For the purposes of promoting an understanding of the principles of the invention, reference will now be made to the embodiments illustrated in the drawings, which are described below. It will nevertheless be understood that no limitation of the scope of the invention is thereby intended. The invention includes any alterations and further modifications in the illustrated device and described methods and further applications of the principles of the invention, which would normally occur to one skilled in the art to which the invention relates. Moreover, the embodiments were selected for description to enable one of ordinary skill in the art to practice the invention.

The measurement arrangement according to FIG. 1 includes a probe 10 that can be inserted into subcutaneous tissue for obtaining a sample liquid, a sensor system 12 for detecting components in the sample liquid, an evaluation and control unit 14 for processing the sensor signals and controlling the measurement process as well as optionally an output unit 16 and an interface 18 to display or transmit the measured results. The probe 10 can be loaded in a known manner with perfusion fluid (microdialysis, microperfusion) or be placed under negative pressure (ultrafiltration) in order to collect the sample liquid.

Figure 2:
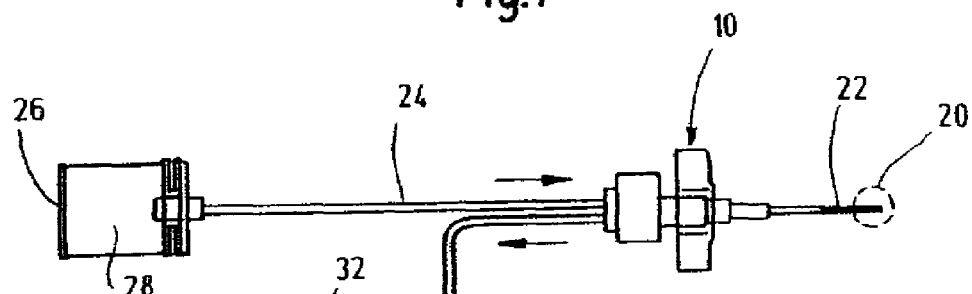
FIG. 2 shows a schematic representation of a microdialysis system as a measuring arrangement.

FIG. 2 illustrates in more detail a microdialysis system for continuous sample collection and measurement data recording. The microdialysis probe 10 has a double-lumen membrane catheter 22 which is located in the tissue 20. The catheter 22 can be rinsed with a perfusion liquid 28 from a liquid reservoir 26 via a feed line 24. The perfusion liquid 28 may comprise any suitable solution, such as physiological saline, for example. The return line 30 of the dialysis probe 10 runs through a peristaltic or roller dosage pump 32 to a collecting vessel 34. A flow measuring cell 36 of the probe 10 may be arranged extracorporeally in the return line 30. The measuring cell 36 detects the concentration of the sought-after analyte in the dialysate, such as glucose, for example, and a reference or control substance, for example, by means of an electrochemical measurement.

Figure 3:
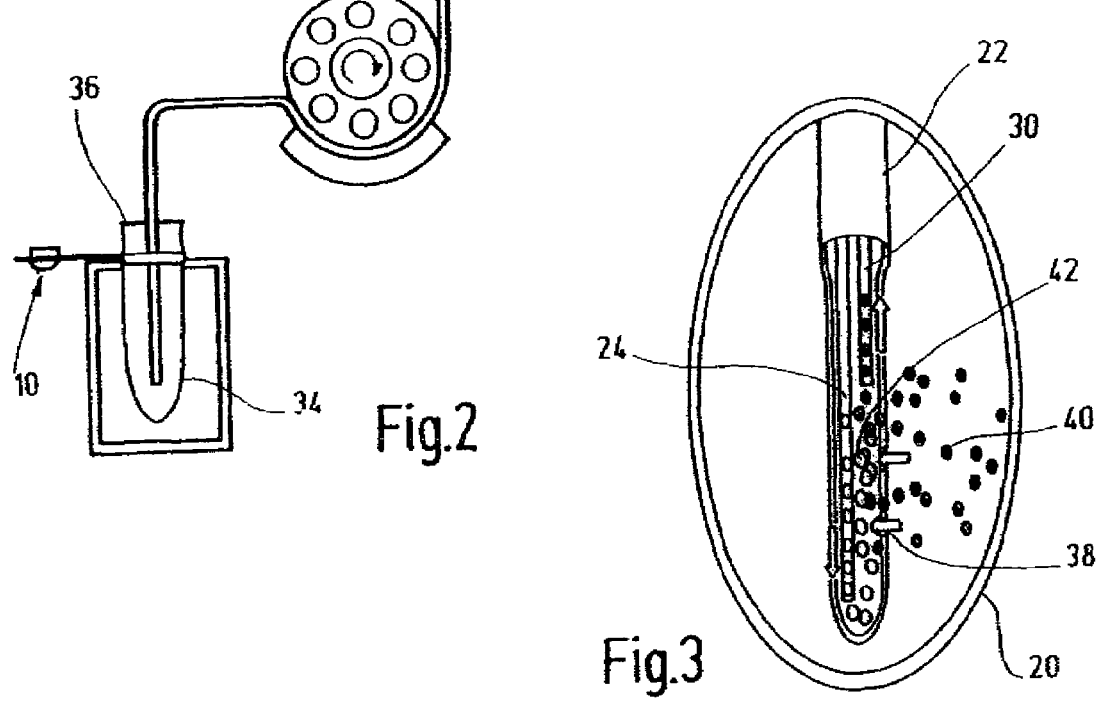
FIG. 3 shows a probe of a microdialysis system according to FIG. 2 in a partially enlarged view.

The mode of operation of the microdialysis probe 10 can be seen in more detail in FIG. 3. The distal end of the catheter 22 has a dialysis membrane 38 which is embedded in the tissue 20 such that the perfusate flowing in through the inlet channel 24 is loaded through the semi-permeable membrane with constituents 40 from the intercellular tissue. The porosity of the membrane 38 is dimensioned so that the metabolic products to be measured, such as glucose, lactate and pyruvate, for example, can pass into the perfusate almost without resistance, and larger molecules are held back. Suitable alternatives may be utilized, such as microperfusion, for example. In the case of microperfusion, there may be no membrane, and the inner space of the probe 10 may be directly coupled to the tissue via perforations in the wall. In both cases the collected sample liquid 42 is aspirated through the mouth of the return channel 30, which is proximally set back from the outlet opening of the line 24.

However, due to various circumstances and in particular to local changes and transport resistances and perfusion rates, the glucose concentration in the dialysate or effusate is not equal to that of the glucose content in the tissue fluid. In order to remedy this situation the sensor unit 10, together with the evaluation unit 14, is designed to additionally determine the concentration of an endogenous reference or control substance in order to carry out a compensation for effects which falsify the measurement. Generally, the glucose concentration in capillary blood is regarded as a "gold standard" which can be determined by spot measurements using known tests.

Figure 4:
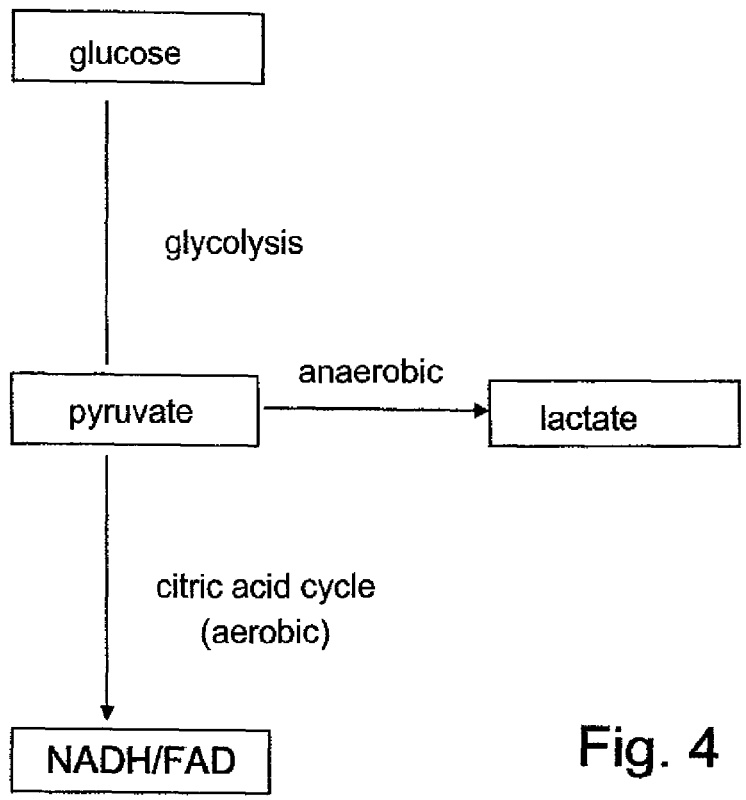
FIG. 4 shows a greatly simplified reaction scheme of glucose processing in body cells.

One aspect concerns the correction of the test value for glucose on the basis of the concentration ratio of lactate to pyruvate in the sample liquid. The background to this is glucose processing in the tissue cells is illustrated in a greatly simplified manner in FIG. 4. Glucose is degraded by glycolysis to pyruvate which can in turn be utilized in an aerobic process with a high energy yield in which the largest possible number of H atoms (in the form of $NADH/H^+$ and $FADH_2$) are obtained which react with oxygen to form water and ATP (citrate cycle). Under anaerobic conditions pyruvate is degraded to lactate in a competing metabolic pathway. This process generates less energy so that the cells have to locally process more glucose to cover their energy requirements. The compensation method, which is elucidated in more detail in the following, is based on the idea that when lactate increases, an exceptional case is present which indicates that the general glucose concentration in the body is higher than the local concentration in the probe environment. Such local changes could, for example, result from the insertion of the probe, or from probe movements, in the tissue.

Figure 5:
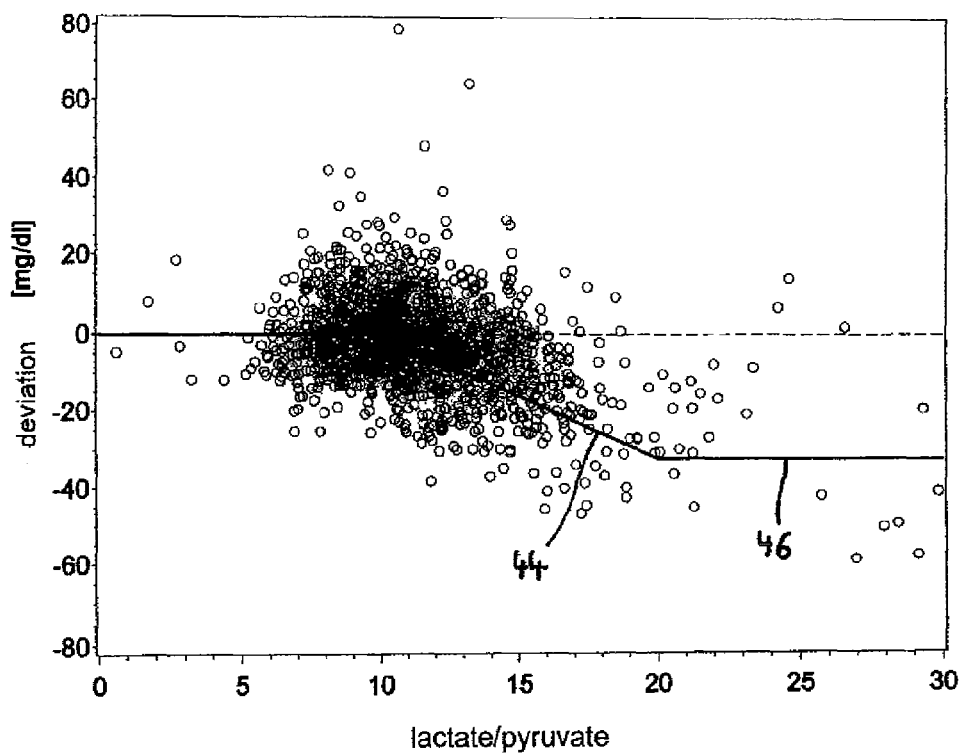
FIG. 5 and FIG. 6 show empirical measurement data of microdialysis examinations using lactate/pyruvate compensation curves.

FIG. 5 shows a measurement diagram in conjunction with an embodiment of a proposed compensation curve. The deviation or difference of the glucose values measured in parallel for sample liquid and blood is plotted against the ratio of lactate to pyruvate in the sample liquid. The aim of the compensation is to reduce the deviation compared to the values in blood. For this purpose, a correction calculation is performed in the evaluation unit which is such that a linear correction is carried out at a concentration ratio of lactate/pyruvate between about 10:1 and about 20:1 (curve section 44) and that the test value for glucose is corrected by a constant above a concentration ratio of about 20:1 (curve section 46). This constant results directly from FIG. 5 by the amount for the abscissa value for section 46.

Figure 6:
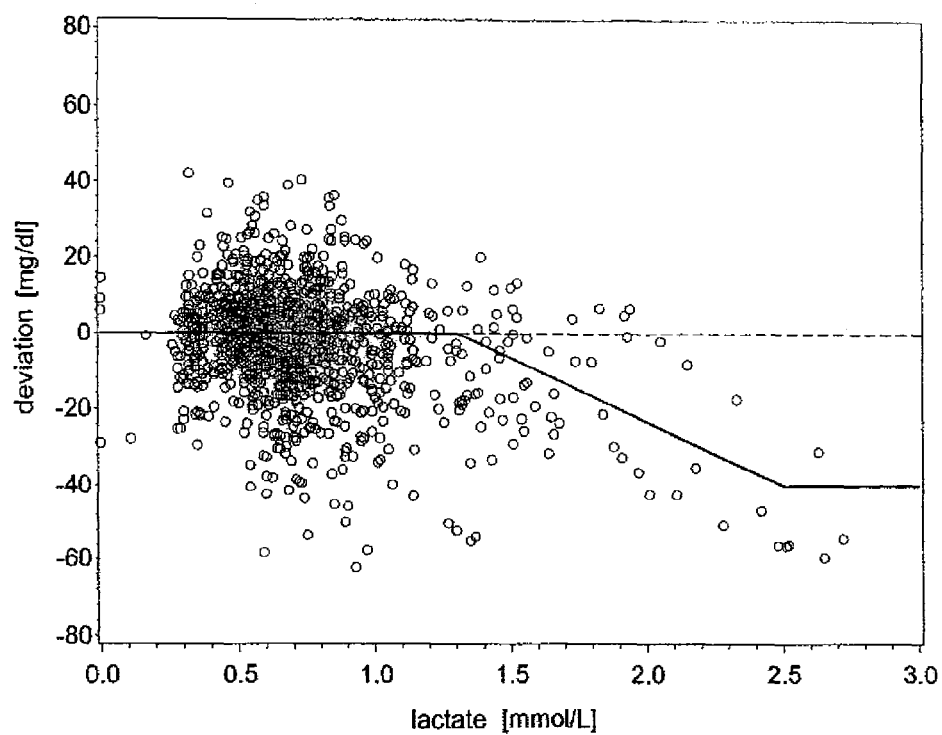

FIG. 6 shows a measurement diagram in conjunction with an embodiment of a proposed compensation curve when only lactate is used as a reference substance. The deviation or difference of the glucose values measured in parallel for sample liquid and blood is plotted against the lactate content in the sample liquid. In order to reduce the deviation compared to the values in blood, a linear correction is carried out at a lactate content between about 1.3 and about 2.5 millimoles per liter whereas the test value for glucose is corrected by a constant when the values of the lactate content are higher than this range. The constant results from FIG. 6 by the amount of the abscissa value of the line of best fit in the upper range.

With reference again to FIG. 1, in ultrafiltration a negative pressure may be applied to a membrane probe 10 by means of a suction pump or suction syringe without feeding in perfusion liquid. As a result, interstitial tissue fluid enters the suction line and is transported to a sensor 12. The semi-permeable membrane of the catheter generally only allows relatively small molecules to diffuse through together with the liquid and thus form a sample liquid which is separate from the tissue fluid. In this case, reactions due to injury can occur in the tissue which result in local changes in the glucose concentration and can be corrected by means of lactate/pyruvate measurements in the sample liquid.

Figure 7:
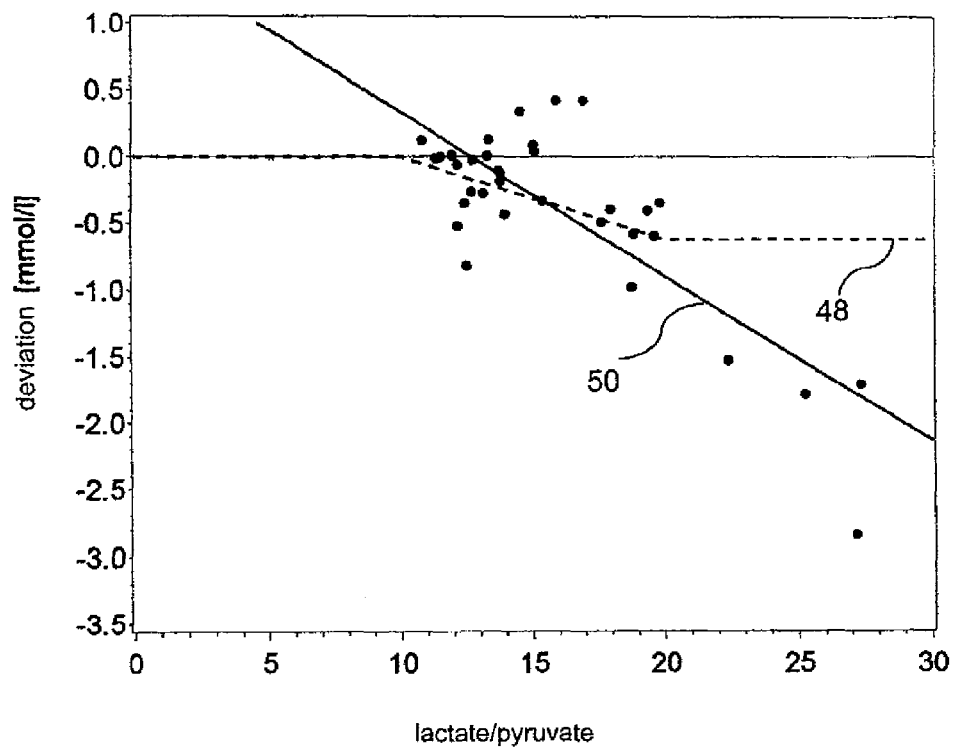
FIG. 7 shows a measurement diagram corresponding to FIG. 5 for an examination by means of ultrafiltration.

FIG. 7 shows test values obtained by ultrafiltration in which the difference between the detected glucose value in the sample liquid and comparative measurements in blood is plotted as the ordinate against the ratio of lactate to pyruvate. The dashed correction curve 48 corresponds to the compensation elucidated above in connection with FIG. 5. It is also possible to only carry out a linear correction corresponding to the continuous line 50 for example in a concentration range between about 10:1 and about 30:1 lactate/pyruvate wherein the slope of the compensation curve was obtained by a fit to the test values.

According to an embodiment of the invention, test values for ions that are kept very constant in the tissue, such as $Na^+$ ions, for example, are detected as an endogenous ionic reference substance, in addition to the glucose values in the sample liquid. In this case, it is assumed that $Na^+$ in the tissue fluid remains substantially constant independently of the glucose processing and that a simultaneous measurement of glucose and sodium ions in the sample liquid can thus be used to deduce the transport or flow resistances in the sample collection. In the example, the recovery rate is defined as the concentration ratio of the respective substance in the tissue fluid and sample liquid. With reference to FIG. 1, the evaluation unit 14 has an evaluation routine 52 for the ionic reference correction which determines the recovery rate $R_{GLU}$ for glucose from a non-linear relationship with the recovery rate $R_{REF}$ for the ionic reference substance ($Na^+$) and thus corrects the test value for glucose.

In particular the evaluation program 52 determines the recovery rate $R_{GLU}$ for glucose from the relationship $$1 - R_{REF} = (1 - R_{GLU})^k \quad (1)$$

in which k is a predetermined value.

The recovery rate $R_{REF}$ for the reference substance is determined as a ratio from the test value for the reference substance in the sample liquid and a known constant concentration value in the tissue fluid.

The equation (1) is based on a non-linear model for recovery:

$$\text{recovery} = 1 - \exp\left[-\frac{1}{Q \cdot W_{tot}}\right] \quad (2)$$

in which Q denotes the flow rate of perfusion and $W_{tot}$ denotes the total resistance as a function of the transport resistances of dialysate, membrane and tissue.

From equation (2) it firstly follows that:

$$\frac{1}{\ln(1 - \text{recovery})} = -QW_{tot} \quad (3)$$

i.e. a logarithmic transformation results in a linear dependence on the flow rate.

A factor k is now sought after which characterizes the ratio of the total resistances for glucose and sodium for a certain dialysis membrane:

$$W_{tot}(\text{glucose}) = k\, W_{tot}(\text{sodium}).$$

This factor k can be estimated with the aid of in vivo studies and in vitro data from equation (3) by forming the quotient.

The factor k is a function of the resistances i.e. in practice a function of the flow rate, membrane and interstitium properties:

$$k = \frac{W_{tot}(glu)}{W_{tot}(Na)} = \frac{\ln(1 - \text{recovery}(Na))}{\ln(1 - \text{recovery}(Glu))}$$

In vivo studies have shown that the influence of the membrane and the physiological environment (determined by osmotic effects) can also be modeled and enables an additional correction of the recovery.

If k is known, then the relationship between recovery (glucose) and recovery (sodium) can be derived from equation (2) as follows:

$$\begin{aligned}
1 - \text{recovery}(Na) &= \exp\left[-\frac{1}{QW_{tot}(Na)}\right] \quad (1)\\
&= \exp\left[-\frac{k}{QW_{tot}(Glu)}\right]\\
&= \exp\left[-\frac{1}{QW_{tot}(Glu)}\right]^k\\
&= [1 - \text{recovery}(Glu)]^k
\end{aligned}$$

Figure 8:
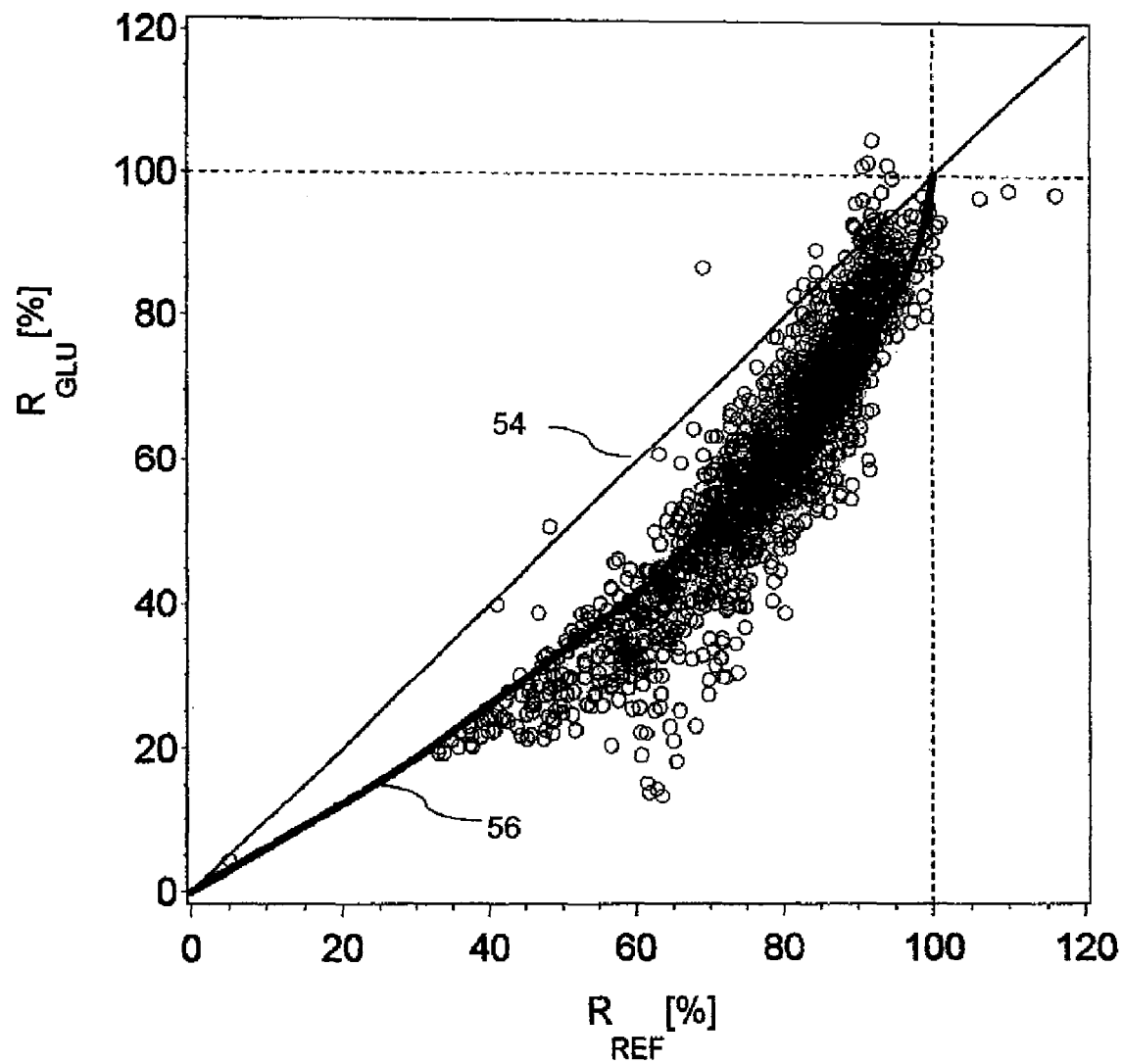
FIG. 8 shows a measurement diagram of the glucose and sodium recovery by means of microdialysis using a calculated compensation curve.

FIG. 8 shows a diagram of the test values of the glucose recovery rate plotted against the $Na^+$ recovery rate. In addition a proportional relationship between the recovery rates, represented by the line 54, and the compensation curve 56 according to the first equation set forth above, is shown in the diagram. It can be clearly seen that the proportional or linear relationship according to line 54 is not confirmed by the test values whereas the compensation curve 56 runs positively curved completely below the bisecting line and thus correctly describes the empirical measurements.

Thus, the compensation curve 56 can compensate for a variation in the recovery by also appropriately correcting the value for glucose on the basis of a changing $Na^+$ recovery. In order to take into account different flow rates, the compensation curve 56 could be compressed by an additional factor which thus takes into consideration the fact that a 100% recovery cannot be reached due to the high throughput.

Any suitable substance, such as $Na^+$, for example, may be utilized as a reference substance to correct for metrological substance. Any suitable substance, such as lactate/pyruvate, for example, may be utilized as a reference substance to correct for locally-related deviations of the test value for glucose in the sample liquid from the actual glucose concentration in the tissue.

In embodiments, the signaling of a malfunction of the measuring arrangement by a signal transmitter when a threshold value of the test value for the reference substance is exceeded may be included in the probe 10.

While this invention has been described as having an exemplary design, the present invention may be further modified within the spirit and scope of this disclosure. The application is intended, therefore, to cover any variations, uses, or adaptations of the invention using its general principles. Further, this application is intended to cover such departures from the present disclosure as come within known or customary practice in the art to which this invention pertains.

The invention claimed is:

1. A method for determining glucose concentration in a tissue fluid in a body, the method comprising the steps of:
   measuring a glucose concentration in a sample of the tissue fluid obtained by a technique selected from the group consisting of microdialysis, microperfusion, and ultrafiltration;
   measuring a concentration of at least one reference substance in the sample of the tissue fluid; the at least one reference substance including lactate and pyruvate;
   determining the glucose concentration of the tissue fluid in the body based upon the measured concentration of the at least one reference substance and glucose in the sample of the tissue fluid.

2. The method as set forth in claim 1 further including the step of determining a concentration ratio of lactate to pyruvate in the sample of the tissue fluid in order to determine the glucose concentration in the tissue fluid in the body.

3. The method as set forth in claim 2 further including the step of utilizing a linear correction factor to determine the glucose concentration in the tissue fluid in the body when the concentration ratio of lactate to pyruvate in the sample of the tissue fluid is within the range between about 10:1 to about 20:1.

4. The method as set forth in claim 2 further including the step of utilizing a constant to determine the glucose concentration in the tissue fluid in the body when the concentration ratio of lactate to pyruvate in the sample of the tissue fluid is about 20:1.

* * * * *